(12) United States Patent
Zohar

(10) Patent No.: US 9,318,013 B2
(45) Date of Patent: Apr. 19, 2016

(54) VIBRATING, PULSE-MONITORED, ALARM BRACELET

(71) Applicant: Tedi Zohar, Long Beach, CA (US)

(72) Inventor: Tedi Zohar, Long Beach, CA (US)

(73) Assignee: Tedi Zohar, Long Beach, CA (US)

( * ) Notice: Subject to any disclaimer, the term of this patent is extended or adjusted under 35 U.S.C. 154(b) by 180 days.

(21) Appl. No.: 13/918,945

(22) Filed: Jun. 15, 2013

(65) Prior Publication Data

US 2014/0111340 A1 Apr. 24, 2014

Related U.S. Application Data

(60) Provisional application No. 61/795,745, filed on Oct. 24, 2012, provisional application No. 61/848,394, filed on Jan. 2, 2013, provisional application No. 61/855,222, filed on May 10, 2013.

(51) Int. Cl.

| | |
|---|---|
| *G08B 21/00* | (2006.01) |
| *G08B 21/06* | (2006.01) |
| *A61B 5/024* | (2006.01) |
| *A61B 5/00* | (2006.01) |
| *A61B 5/0245* | (2006.01) |
| *A61B 5/16* | (2006.01) |

(52) U.S. Cl.
CPC ............... *G08B 21/06* (2013.01); *A61B 5/024* (2013.01); *A61B 5/02438* (2013.01); *A61B 5/02455* (2013.01); *A61B 5/16* (2013.01); *A61B 5/681* (2013.01); *A61B 5/7455* (2013.01)

(58) Field of Classification Search
CPC ........................................................ G08B 21/06
USPC ................................... 340/575, 576; 180/272
See application file for complete search history.

(56) References Cited

U.S. PATENT DOCUMENTS 6,445,303 B1 * 9/2002 Aryeh ........................... 340/575

* cited by examiner

*Primary Examiner* — Jeffery Hofsass

(57) ABSTRACT

A vibrating pulse monitored alarm bracelet consists of control panel/display/capacitive touchscreen, a flash memory to collect and communicate data, two rechargeable batteries which serve as the power source for the device, sensors to collect pulse rate data, vibrating pads to provide silent, electric pulse stimuli, and a neoprene band to secure the device to its wearer.

6 Claims, 6 Drawing Sheets

VIBRATING, PULSE-MONITORED, ALARM BRACELET

CROSS-REFERENCE TO RELATED APPLICATIONS

61/795,745; 61/848,394; 61/855,222

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

FIELD OF THE INVENTION

The present invention is in the technical field of alarm bracelets. More particularly, the present invention is in the technical field of pulse-monitored, silent alarm bracelets. This invention relates to a drowsiness warning system which monitors the wearer's pulse rate and activates the vibration mode when the wearer's pulse rate falls below a calculated, predetermined level.

BACKGROUND OF THE INVENTION

Conventional alarms such as alarm clocks, cell phones, digital watches are only useful when set to a certain time specification. However, what if sleep overcomes a person who has neglected to set the traditional wake up device? Furthermore, what if sleep overwhelms one who is in acting in a situation where sleep is inappropriate. For example, a deployed soldier standing guard on an overnight watch would jeopardize his own life as well as the life of others if he succumbs to sleep. For the soldier to anticipate the exact moment when sleep will occur is impossible. Therefore, to predict sleep and be prepared by setting an alarm is not feasible. For the safety of the soldier and his/her team members, the soldier needs assistance to stay awake. This is the case for many professions: military, nursing, transportation, education, security and criminal justice, as well as, the general population who may engage in an activity that will put a person or others in harm's way if sleep occurs. If a device can detect physical manifestations of sleep and respond to that change, unwanted sleep can be avoided.

SUMMARY OF THE INVENTION

The present invention is a bracelet that monitors the average pulse rate of its wearer; when the pulse slows below the resting heart rate—an indicator of sleep, the bracelet vibrates silently to restore the wearer to the state of being alert. The human heart rate can be affected by many variables. Each individual has a resting heart rate that is unique to that individual. An individual's resting pulse rate can change over a lifetime based on how physically active the person is, the amount of stress one is facing, and numerous other weighted factors. The average range of a resting heart rate ranges from 50 to 85 beats per minute. Another factor that alters heart rate is the onset of sleepiness.

For a majority of the population, the onset of sleep drops the pulse rate between 55 to 65 beats per minute. The average reduction of pulse rate during sleep is 8%. However, if that percentage of decrease has been reached, the awareness and alertness of the individual has been compromised. Therefore, the warning to the individual must occur before the full onset of sleep. To review the function of this device, each individual will calibrate the device. For example, the individual will attach the bracelet to his/her wrist. Once the device is activated, it will calibrate to the average pulse rate of the individual. If the pulse rate falls below the specified percentage below the wearer's average pulse rate; then, the silent alarm triggers and vibration waves stimulate the wearer's arm. The sensation is like that of a limb that "falls asleep" and tingles. This alerts the wearer of the onset of sleep and the individual may then take the appropriate precautions for safety in his or her given situation.

Furthermore, the strength of the vibration necessary for effectiveness will vary from individual to individual. Therefore, the vibration mode will be adjustable to be customized to the need of each wearer. There will be 10 levels of vibration that will activate at a specified level then escalate to the desired full effect for the individual as to not startle the individual. The device will activate 3 levels below the desired "awake" level. For example, a young female may select the desired vibration level 6. As the device is activated by the reduction of pulse rate, the device will activate at level 3 and build steadily to level 6 to restore the individual to full awareness. For another example of custom vibration, a middle-aged male may preset the vibration level to 10. For him, the device would activate at level 7 and build to level 10 for maximum individual effectiveness.

When an individual first attaches the band to his/her wrist, he/she will engage the capacitive touchscreen and press the option to calibrate. The device will detect and monitor the wearer's average heart rate throughout the duration of device usage. As soon as the device calibrates, it will cue the wearer to set the vibration level. The device will fire at level 1; then the wearer can increase level for individual optimum effectiveness.

If the device does not receive input for pulse detection within 90 seconds, the device hibernates to save battery life. The device will retain the settings for this individual until another wearer calibrates the device for his/her use. When the device is reattached to the wearer, the pulse is detected and the device restores to active state.

Furthermore, a flash memory records the time and date of each "fired" vibration warning of the device as a record of the wearer's sleepiness patterns. When the device is calibrated for a new wearer, the calibration is reset and the device will begin recording new data for the new wearer.

Due to the device's bluetooth capabilities, the device can share information with other personal devices. This can also be utilized for audibly signaling to a driver through a phone, GPS, or Bluetooth capable audio/stereo car systems.

There is a second mode that the wearer can select when he/she is in a situation when sleep is appropriate and desired or when there is no danger that will result from the onset of sleep. For example, a nurse who is working a double shift has an hour break. The nurse may choose to sleep briefly to revive himself/herself for the next phase of the shift. He/she can set his/her device to sleep mode to ensure that he/she is restored to full awareness before his/her shift resumes. Since the vibration alarm is silent, no patient or coworker will be disturbed by the use of the device. When the bracelet is set to this mode, the wearer can set the silent vibrating alarm for a desired wake up time; or, the wearer can simply refer to the device as a digital clock.

The device is powered by a rechargeable, lithium, 3V, button batteries. The batteries are rechargeable by two systems. The first system available will recharge the device externally through a battery charging micro-USB port that pulls energy through a connector which can be powered from an electrical outlet or through a car charging adapter. The second option also utilizes the micro-USB port but pulls energy from an external solar powered charger. The use of rechargeable energy allows the device to function with consideration for clean energy processes.

The device is wearable on the wrist. It includes a capacitive touchscreen that navigates and controls this device. Through the navigation screen, the wearer calibrates the device and allows the wearer to establish his/her average pulse rate. Then, the wearer sets the customized vibration level for his/her usage. The programming allows the wearer to select between the "work" and "sleep" modes. There is also a display lock button on the side of the device which houses the micro-USB port. When the display is locked, no programming can be accessed or altered. The neoprene band provides a weatherproof casing to optimize the durability of the device in any climate or territory.

DETAILED DESCRIPTION OF THE INVENTION

Figure 1:
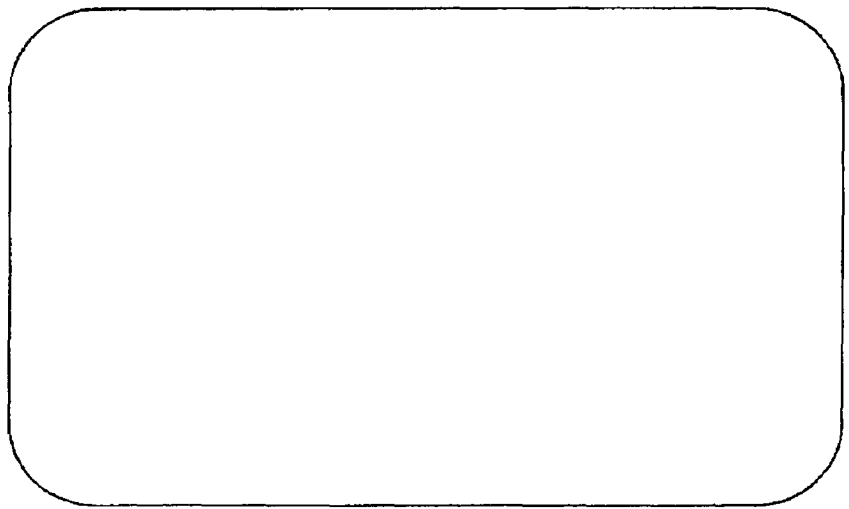
FIG. 1 is a perspective view of the anterior of the vibrating bracelet and the capacitive touchscreen, control panel of the present invention.
Figure 1:
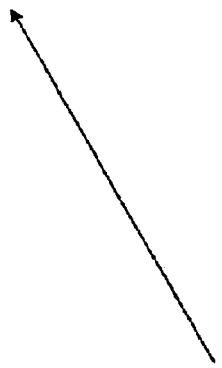
Figure 2:
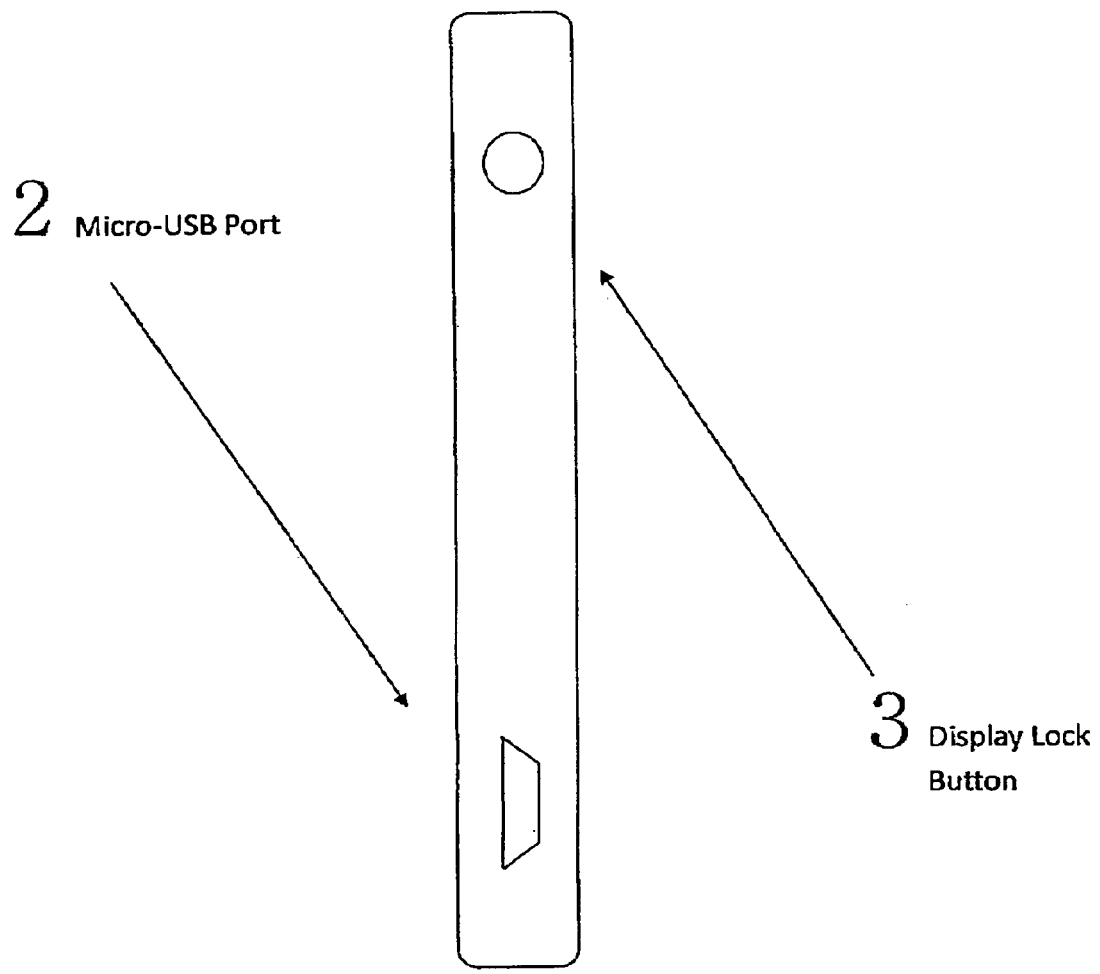
FIG. 2 is a side view of the vibrating bracelet of FIG. 1.

Referring now to the invention in more detail, in FIG. 1 and FIG. 2, there is shown a control panel 1 on which is located the capacitive touchscreen 1, which controls the vibration levels and the time settings as well as the display lock button 3 that locks the operational mode of the present device. The micro-USB port 2 for charging the device and data sharing is located on the same surface as the display lock button 3 as shown on FIG. 2.

In further detail, still referring to the invention of FIG. 1 and FIG. 2, display screen is sufficiently wide and long for comfortable viewing, such as 1 inch by 1½ inches. The button 3 is sized appropriately to be unobtrusive, while the micro-USB port 2 is the standard industry specification.

The construction details of the invention as shown in FIG. 1 and FIG. 2 are that the present device may be made of sufficiently rigid and strong material such as high-strength plastic, metal, and the like. Further, the various components of the display control panel can be made of different materials.

Figure 3:
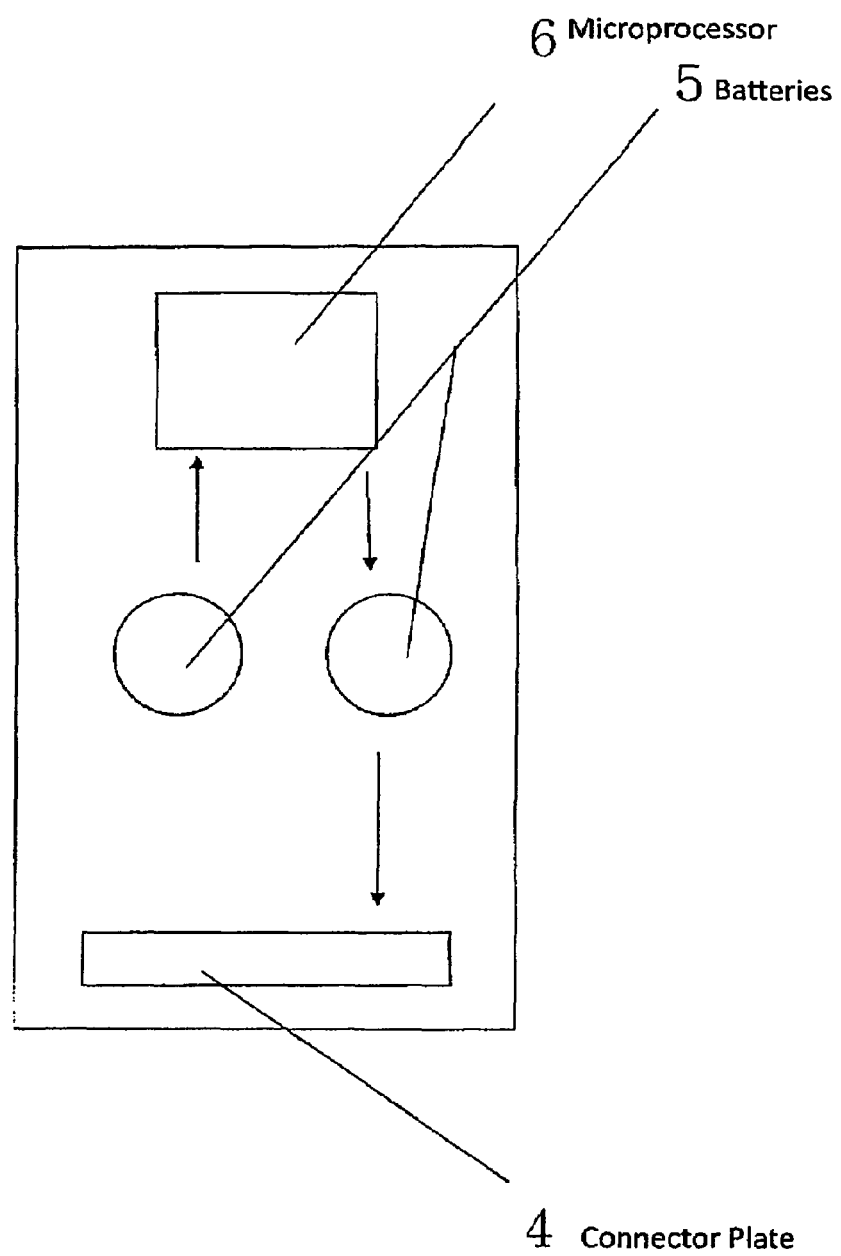
FIG. 3 is a perspective view of the interior mechanism of the alarm bracelet of the present invention.
Figure 4:
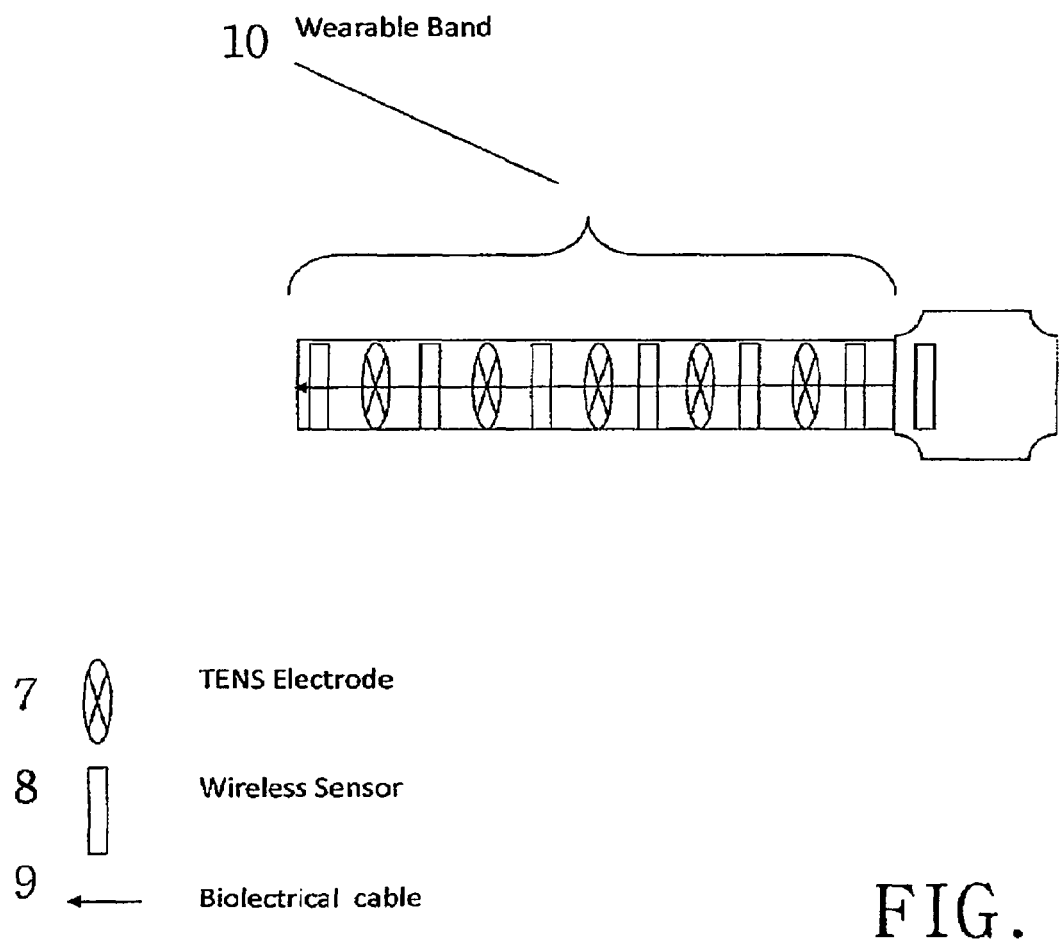
FIG. 4 is an enlarged view of the vibrating pads and sensors of FIG. 6.

Referring now to FIG. 3 and FIG. 4, there is shown the internal components of the device. The connector plate 4 is the transmitter that emits the electronic pulse to the vibrating pads 7 on FIG. 4. The wireless sensor 8 collects the pulse rate data and transmits it to the microprocessor for monitoring. The rechargeable batteries 5 supply power to the control panel (FIG. 1) and the vibrating mechanism FIG. 3 and FIG. 4. The rechargeable batteries 5 are chargeable through a battery charging port that pulls energy through a micro-USB port 2 which can be powered from an adapter by an electrical outlet or through a car charging port. Again referring to FIG. 3, the microprocessor 6 is the operating system of this present device.

In more detail, still referring to the invention in FIG. 3 and FIG. 4, the connector plate 4 is approximately ¾ inch by ¼ inch. The batteries 5 are 3V, rechargeable, lithium, button batteries. The microprocessor 6 is approximately ¾ inch by ½ inch. In addition, the vibrating pads 7 of FIG. 4 are dispersed equidistant alternating with the wireless sensors 8 connected within and throughout the neoprene band 10 with bioelectrical cable 9 shown in FIG. 4.

The construction details of the invention as shown in FIG. 3 and FIG. 4 are that the present device may be made of sufficiently rigid and strong material such as high-strength plastic, metal, silicone, and the like. The button batteries 5 in FIG. 3 are rechargeable lithium with 3V.

Figure 5:
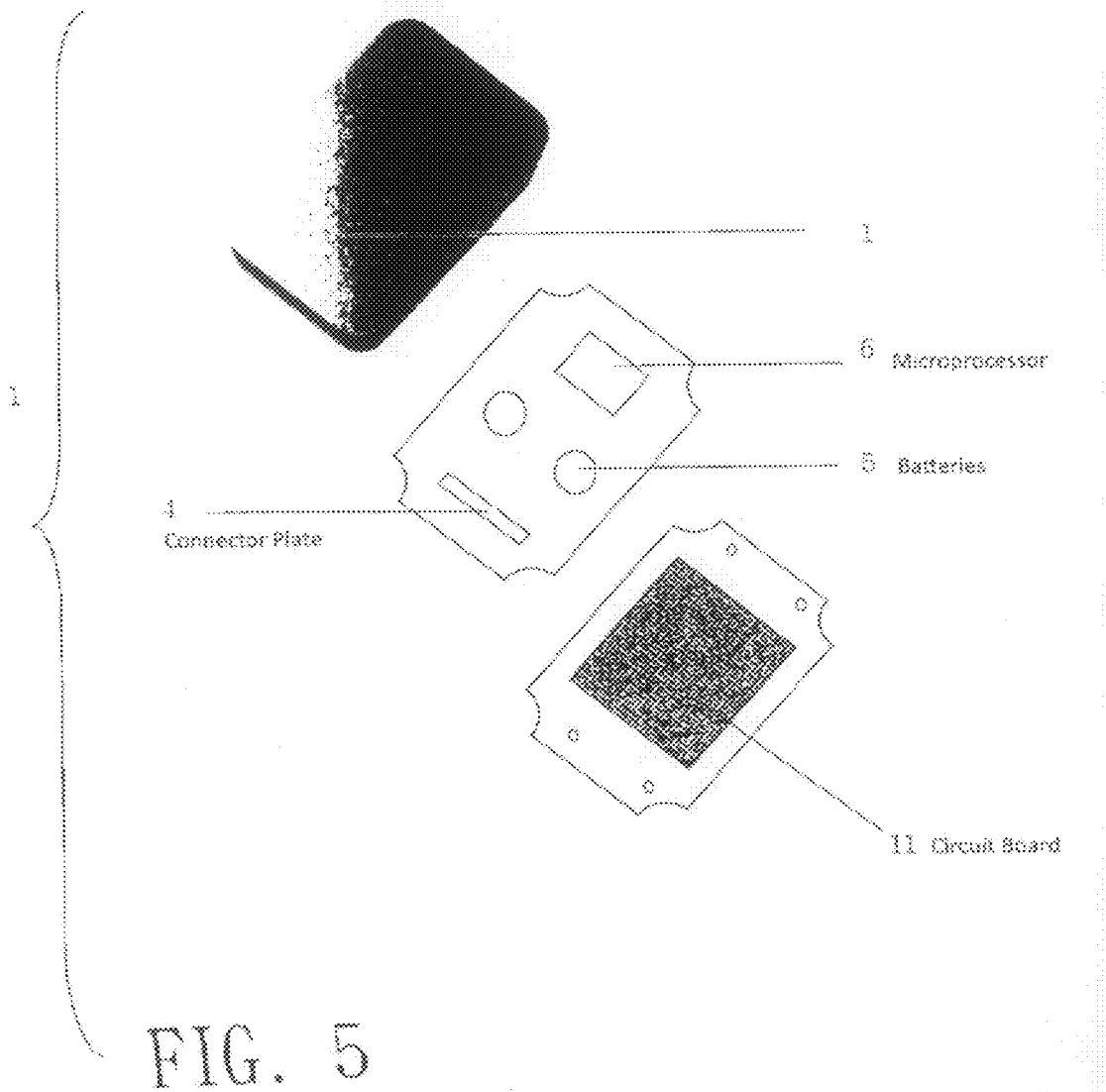
FIG. 5 is the expanded perspective view of FIG. 1, FIG. 3, and FIG. 4.

Furthermore, the various components of the inner mechanism can be made of different materials. Referring now to FIG. 5, there is shown the various layers of the present device: capacitive touchscreen 1, the connector plate 4, the rechargeable, lithium button batteries 5, the microprocessor 6, and the circuit board 11 which is embedded in the inner casing of the control panel of the present device.

Figure 6:
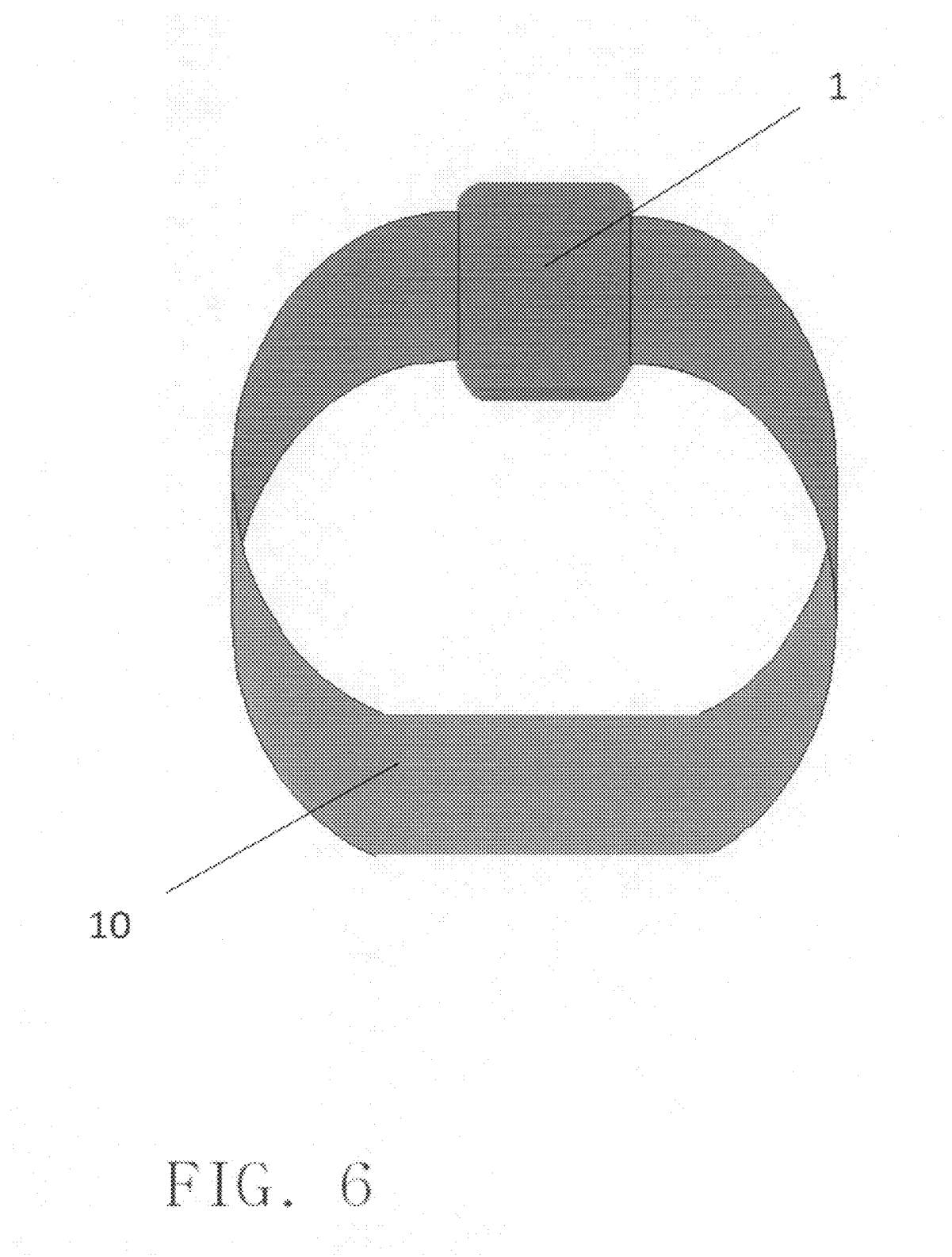
FIG. 6 is the general 3-D image of the device.

Referring now to FIG. 6, there is shown the 3D, external, perspective view of the vibrating, pulse-monitored, alarm bracelet as a whole: capacitive touchscreen 1 and the bracelet band 10 which fastens the device to the wearer and protects mechanisms of FIG. 4.

In more detail referring to FIG. 6, the band of the device has a width of 1-2 inches, a length of 6-9 inches and is composed of neoprene. The band is permanently attached on one side of the device and clasps into the opposite side of the control panel 1 with a box and tongue clasp. The construction details of the invention as shown in FIG. 5 and FIG. 6 are that the present device may be made of sufficiently rigid and strong material such as high-strength plastic, metal, neoprene, and the like. Furthermore, the various components of the device can be made of different materials.

The advantages of the present invention include, without limitation, that it is lightweight and dependable. The band of the device is comfortable, well-fitting, and adjustable, available in four sizes to fit all. The device is easy to set with two modes of operation. The device is weather-proof and can function without failing in extreme temperatures. Moreover, the present device is sweat/water resistant and with certain specifications waterproof with a sufficient depth rating. The device has application for all sectors of society—civilian to military, or in any situation when it is vital for one to stay awake and alert.

In broad embodiment, the present invention is a vibrating pulse monitoring alarm device that also has a vibrating alarm clock mode.

While the foregoing written description of the invention enables one of ordinary skills to make use of what is considered presently to be best the mode thereof, those of ordinary skill will understand and appreciate the existence of variations, combinations, and equivocations of the specific embodiment, method, and examples herein. The invention should therefore not be limited by the above described embodiment, method, and examples, but by all embodiments and methods within the scope and spirit of the invention as claimed.

What is claimed is:

1. A Vibrating, Pulse-Monitored, Alarm Bracelet monitors the heart-rate for its wearer when their pulse slows to a calculated rate below the wearer's average, the method comprising:

Detecting a resting pulse rate that is an indicator of drowsiness or the onset of sleep, wherein the device activates silent, bioelectric pulse stimuli at an accelerating rate from levels of low to high from the wearer's customized, predetermined level which is set when the user calibrates the device at the initiation of wearing the device, which includes vibrating pads, wireless heartrate sensors, bioelectrical cable, a microprocessor, flash memory, a capacitive touchscreen, a control panel, rechargeable, lithium batteries, a micro-USB port, Bluetooth capabilities.

2. The Vibrating, Pulse-Monitored, Alarm Bracelet according to claim 1, wherein the embodiment of the device functions as follows when worn by its wearer:
   a) A capacitive touchscreen activates and signals to the microprocessor to engage heart rate sensors;
   b) Wireless heart rate sensors gather pulse rate data and transmit it to the microprocessor
   c) A microprocessor begins calibration establishing the baseline resting heart rate for the wearer signaling the pulse information to the capacitive touchscreen;
   d) A Capacitive touchscreen then prompts the wearer to adjust and set the level of vibration from the desired initial onset and the desired highest level of vibration;
   e) A Microprocessor records data and begins continual monitoring of pulse data, generating a silent, vibrating alarm through the bioelectric cable to the vibrating pads firing at the wearer's preset level one and increasing to the wearer's preselected high level of vibration if the resting heart rate falls to a rate calculated by a predetermined formula of a percentage drop of beats below the wearer's resting heart rate; when the pulse increases to or above the resting heart rate; the vibration ceases,
   f) The control panel allows for the level of vibration or heart rate level to be modified at any time during usage; and
   g) A flash memory records data of when the device alarms.

3. The Vibrating, Pulse-Monitored, Alarm Bracelet according to claim 1 wherein the capacitive touchscreen is the control panel and information display unit of the device to navigate and set the specifications of the device and retrieve information.

4. The Vibrating, Pulse-Monitored, Alarm Bracelet according to claim 1 wherein the micro-USB port is used to charge the rechargeable, lithium batteries and can download from the device or upload data to the device.

5. The Vibrating, Pulse-Monitored, Alarm Bracelet according to claim 1 wherein the Bluetooth capabilities of the device permits the sharing of data and interaction with other Bluetooth enabled devices.

6. The Vibrating Pulse-Monitored, Alarm Bracelet according to claim 2, wherein the device functions within two separate operational Modes a) Modes: WORK and SLEEP
   1) When set to WORK Mode, the present device functions to monitor the wearer's pulse rate,
   2) When set to SLEEP Mode, the present invention disables the pulse monitoring feature and functions as a digital clock that can be set for a specific time as a silent, vibrating alarm clock, and
   A feature for sound in addition to vibration which can be selected in both Modes through the control panel on the capacitive touchscreen.

* * * * *